(12) United States Patent
Gitis et al.

(10) Patent No.: US 6,363,798 B1
(45) Date of Patent: Apr. 2, 2002

(54) METHOD AND DEVICE FOR MEASURING FORCES

(76) Inventors: Norm Gitis, 10131 Finwood Dr., Cupertino, CA (US) 95014; Michael Vinogradov, 125 Macdowell Terr., Sunnyvale, CA (US) 94087; Vlad Dorfman, 931 Bermuda Ct., Sunnyvale, CA (US) 94086

( * ) Notice: Subject to any disclaimer, the term of this patent is extended or adjusted under 35 U.S.C. 154(b) by 0 days.

(21) Appl. No.: 09/624,512

(22) Filed: Jul. 24, 2000

(51) Int. Cl.[7] .............................. G01L 5/04; G01L 5/00
(52) U.S. Cl. ............................ 73/862.391; 73/862.381; 73/862.632; 73/862.633
(58) Field of Search ..................... 73/862.391, 862.632, 73/862.633, 862.634, 862.627, 862.637, 862.381

(56) References Cited

U.S. PATENT DOCUMENTS

| 3,577,779 A | * | 5/1971 | Laimins | 73/633 |
| 5,795,990 A | | 8/1998 | Gitis et al. | 73/9 |
| 6,038,933 A | * | 3/2000 | Meyer | 73/862.045 |

* cited by examiner

Primary Examiner—Benjamin R. Fuller
Assistant Examiner—Andre Allen
(74) Attorney, Agent, or Firm—Ilya Zborovsky

(57) ABSTRACT

The device of the invention is intended for measuring a loading force and a friction force in a tribological tester. The device consists of two deformation-sensitive sensors for simultaneous equal deformation in two opposite directions for eliminating misbalance created in the measurement system when a single sensor is used. Each sensor is a deformable beam having through longitudinal slots extending in different and non-parallel directions and overlapped within the body of the beam. The sensor deforms in one direction under the effect of a loading force measured by two pairs of strain gauges located on opposite sides of the beam near one end of the beam and in another direction under the effect of a friction force measured by another two pairs of strain gauges located on opposite sides of the beam near the other end of the beam. Two sensors are sandwiched between two plates in a diagonally symmetrical positions so as to transmit forces between both plates and at the same time to ensure limited freedom of movement between both plates to allow deformations caused by the applied forces. One plate may be attached to the loading unit of the tester and another plate may support an upper sample for engagement with the lower sample of the tester.

16 Claims, 5 Drawing Sheets

METHOD AND DEVICE FOR MEASURING FORCES

FIELD OF THE INVENTION

The present invention relates to force measurement technique, in particular to a method and apparatus for measuring friction forces on a friction tester.

BACKGROUND OF THE INVENTION

Tribology is a science of friction, wear, and lubrication on friction surfaces. Many different types of friction testers, tribometers, and other devices for measuring various parameters of friction are known. One such friction tester is disclosed in U.S. Pat. No. 5,795,990 issued to Norm Gitis, et al in 1998. This tester has a lower disk-like test material specimen and an upper rod-like test material specimen or probe which performs orbital motions while being in contact with a stationary lower specimen. A disadvantage of this device is that the upper specimen has a leverage with respect to the point of attachment of the lower specimen, i.e., with respect to its center. As a result, the loading force applied to the lower specimen via the upper probe, as well as the reaction force applied to the probe from the lower specimen create an unbalanced momentum and deformations in the force measurement system. Similar problem occurs in a mechanism for attachment of a bi-directional force sensor in a friction tester, as disclosed in our pending patent application Ser. No. 09/588,054 filed by the same applicants on Jul. 24, 2000.

As shown in FIG. 1, which is a three-dimensional view of a sensor installed in a friction tester for measuring a friction force and other tribological parameters of various materials and lubricants, the device has a sensor 10 formed by a beam 12 flexible in two mutually perpendicular directions for measuring a loading force $F_1$ and a friction force $F_{FR}$. Both ends of the beam are connected or integrally made with rigid end blocks 14 and 16. The end block 16 is rigidly attached to a loading unit 18 of the tester (not shown), while the end block 14 supports an upper specimen or probe 20 which is maintained in contact with a disk-like lower specimen D. The solid end block 14 has a limited freedom of movement to ensure deformation within the range of measurements. Flexibility of the beam 12 in the X-Z plane, i.e., deformations caused by the loading force $F_1$ are allowed due to the provision of a through slot 21 with notches 22 and 24. The notches have a width wider than the width of the slot 21 thus weakening the beam and making it deformable in the area of the notches 22 and 24. Similarly, flexibility of the beam 12 in the Y-Z plane, i.e., deformations caused by the friction force $F_{FR}$ are allowed due to the provision of a through slot 26 with notches 28 and 30. The notches 28 and 30 have a width wider than the width of the slot 26 thus weakening the beam and making it deformable in the area of the notches 28 and 30. The slots 26 and 21 are partially overlapped within the body of the beam 12 so that the beam can be considered as two deformable parallelograms that arranged in two mutually perpendicular planes. Deformations of the beam 12 caused by the loading force $F_1$ in the X-Z plane are measured by two strain gauges 32 and 34. Reference numeral 34 designates the strain gauge located on the other side of the beam. However, the strain gauge 34 itself is not seen in FIG. 1. Similarly, deformations of the beam 12 caused by the friction force $F_{FR}$ in the Y-Z plane are measured by two strain gauges 36 and 38 located on both sides of the beam near the weakened portion on the other end of the beam (only one of these strain gauges 36 is seen in FIG. 1). In more detail the construction of the beam 12 and principle of its operation during friction testing is described in pending U.S. patent application Ser. No. 09/588,054 filed by the same applicants on Jul. 24, 2000.

In the course of testing, the lower specimen D is brought into rotation, e.g., in the direction shown by an arrow R, and then a loading force $F_1$ is applied to the solid end block 16 whereby the upper specimen 20 comes into contact with the lower specimen D. Application of force $F_1$ causes interaction between the upper specimen 20 and the lower specimen D. The aforementioned interaction generates friction force $F_{FR}$ and reaction force $F_R$. Due to flexibility of the beam 12, these forces cause deformations of the beam 12 which are registered by the aforementioned pairs of strain gauges.

However, the friction force $F_{FR}$ generates unbalanced momentum and torsion deformations in the force measurement system. Such asymmetry results in a number of undesired phenomena, such as occurrence of parasitic vibrations generated during rotation of the lower specimen D, tilting of the upper specimen 20, and as a result, limitation in the frequency of rotation, narrowing of test ranges, and inaccuracy of measurements.

OBJECTS OF THE INVENTION

It is an object of the present invention to provide a method and a force measurement apparatus which eliminate an unbalanced momentum and deformation in the force measurement system of the tester, improve accuracy of measurements, broaden the range of test conditions, and prevents such phenomena as parasitic vibrations.

SUMMARY OF THE INVENTION

The device of the invention for force measurement in a friction tester comprises an assembly of two deformation-sensitive sensors for simultaneous equal deformation in two opposite directions for eliminating misbalance created in the measurement system when a tester with a single sensor is used. Each sensor comprises a deformable beam having through longitudinal slots extending in different and non-parallel directions and overlapped within the body of the beam. Each sensor deforms in one direction under the effect of a loading force measured by two strain gauges located on opposite sides of the beam near one end of the beam and in another direction under the effect of a friction force measured by another two strain gauges located on opposite sides of the beam near the other end of the beam. Two aforementioned sensors are sandwiched between two plates in diagonally symmetrical positions so as to transmit forces between both plates and at the same time to ensure limited freedom of movement between both plates to allow deformations caused by the applied forces. One plate is attached to the loading unit of the tester and another supports an upper specimen for engagement with the lower specimen of the tester.

FIGS. 2–4—DETAILED DESCRIPTION OF THE INVENTION

Figure 2:
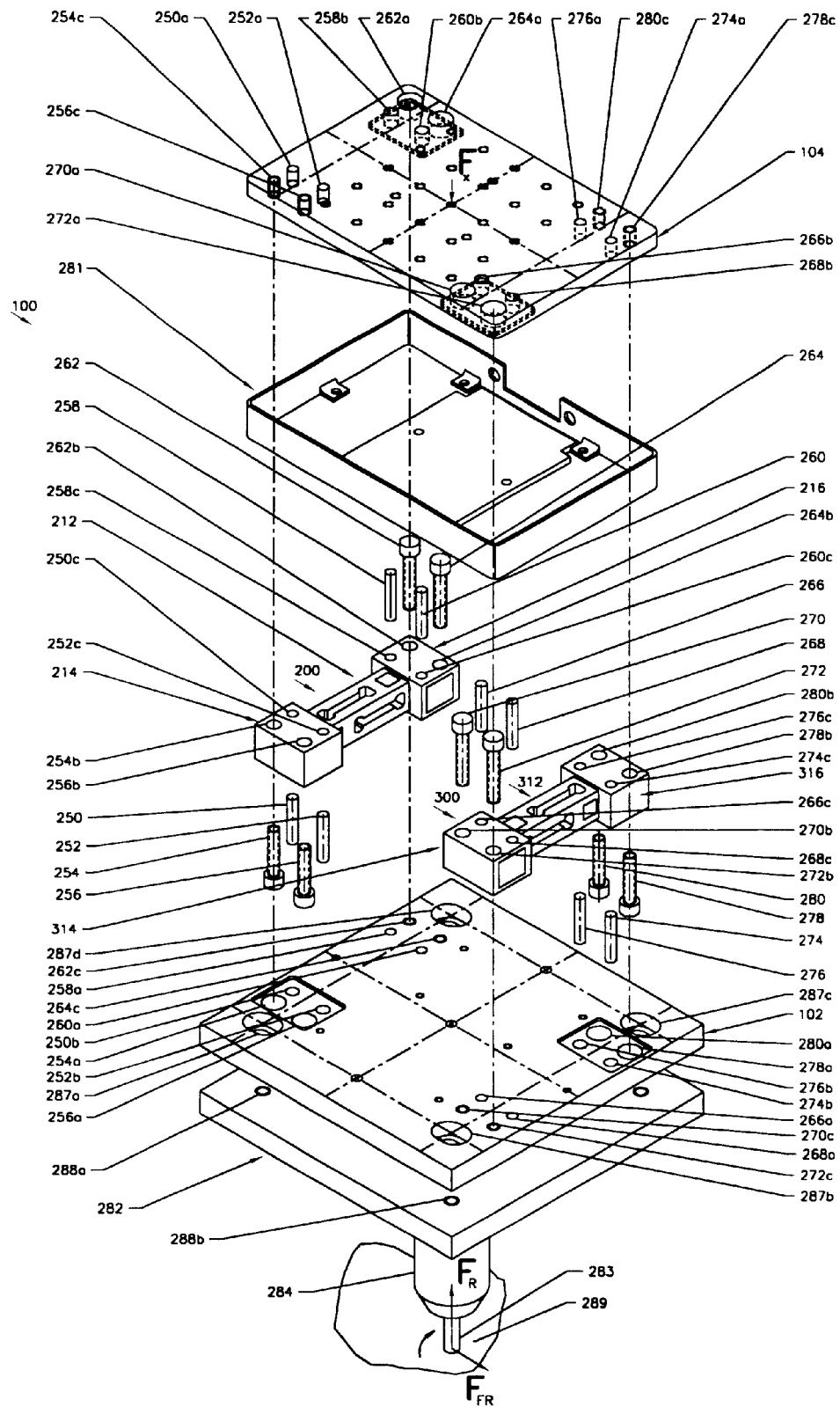
FIG. 2 is a three-dimensional exploded view of a device of the invention for force measurement in a friction tester.

FIG. 2 is a three-dimensional exploded view of a device of the invention for force measurement in a friction tester. As can be seen from this drawing, the device, which in general is designated by reference numeral 100, consists of a lower plate 102 of a rectangular shape, an upper plate 104 which has substantially the same shape and dimensions as the plate 102, and a pair of sensors 200 and 300 sandwiched between the lower plate 102 and the upper plate 104. The upper plate 104 is connected to a loading unit of a friction testing apparatus (not shown), and the lower plate 102 supports a stationary upper specimen, which during testing is maintained in contact with a moveable lower specimen. The specimens will be shown and described later in connection with operation of the device. Both sensors are spaced from each other and are arranged symmetrically diagonally opposite to each other. In other words, the sensor 200 is located in a position turned 180° with respect to the sensor 300.

Each sensor has a construction and function described in detail in U.S. patent application Ser. No. 09/588,054 filed by the same applicants on Jul. 24, 2000. Since both sensors 200 and 300 are identical, for better understanding the principle of the present invention, the description of one of the sensors, e.g., the sensor 200, will now be repeated.

Figure 3:
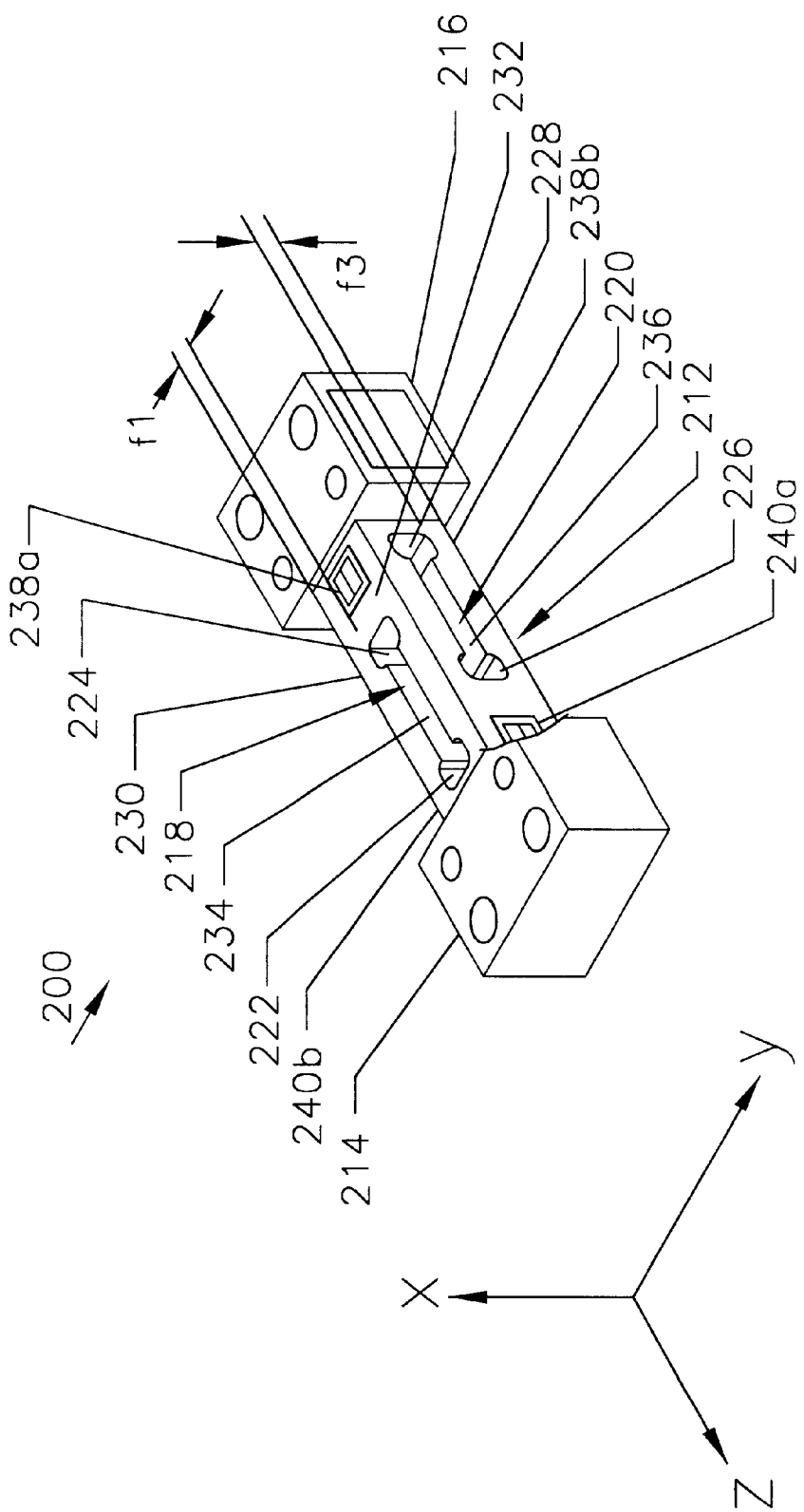
FIG. 3 is a three-dimensional view of a sensor used in the device of FIG. 2.

FIG. 3 is a three-dimensional view of the sensor 200 used in the device of FIG. 2. The sensor comprises a flexible beam 212 of a rectangular cross section with rigid solid end blocks 214 and 216 at both ends for securing the sensor to the upper. and lower plates 104 and 102, respectively (FIG. 2). The beam 212 has two symmetrically shaped through slots 218 and 220 cut in mutually perpendicular directions X and Y, respectively. The slots 218 and 220 partially intersect within the body of the beam 212. Each slot has on its opposite ends a through hole or notch, i.e., notches 222, 224 on the opposite ends of the slot 218 and through notches 226, 228 on the opposite ends of the slot 220, respectively. The notches 222, 224 and 226, 228 are wider than the respective slots 218 and 220.

The distances "$f_1$" and "$f_3$" from the inner walls of the respective notches 222 and 226 to the outer side surfaces 230 and 232 (only the edge of the surface 230 is seen in FIG. 3) of the beam are shorter than the distances to the surface 230 and 232 from the inner walls 234 and 236 of the slots 218 and 220. The thinned portions of the beam 212 impart anisotropic flexibility to the beam required for increasing sensitivity of the sensor. The aforementioned anisotropic flexibility is ensured in the direction perpendicular to the direction of a respective slot and thus coincides with the direction of the force to be measured. In other words, for a force acting in the direction of axis X flexibility will be provided only in the direction of axis X by the notches 226 and 228 of the slot 220, and for a force acting in the direction of axis Y flexibility will be provided only in the direction of axis Y by the notches 222 and 224 of the slot 218.

In fact, the beam 212 with the slots 218 and 220 cut through the body of the beam in two different intersecting directions, which in the embodiment shown in FIG. 3 are two mutually perpendicular directions, can be compared with a pair of mutually overlapped parallelograms combined in one body which will be described later in connection with the operation of the sensor.

Force sensing elements, such as strain gauges 238*a*, 238*b* and strain gauges 240*a*, 240*b* are attached to opposite sides of the beam on mutually perpendicular surface areas at the ends of the beam which are flexible enough (due to provision of the notches) to comply with sensitivity of strain gauges used for measuring deformations and registering the measured deformations with appropriate electronic instrumentation (not shown). Only one strain gage of each pair, i.e., the strain gauges 238*a* and 240*a*, are seen in FIG. 3, while strain gauges 238*b* and 240*b* are not seen and their reference lines reach the edges of their respective sides.

The dimensions of the slots 218, 220 as well as the notches 222, 224 and 226, 228 are chosen in connection with the material of the beam so that deformations caused by the measured forces are reversible without residual deformations and directly proportional to the aforementioned forces. It is understood that the strain gauges 238*a*, 238*b*, 240*a*, 240*b*, should be chosen so as to respond to mechanical deformations caused by measured forces within the entire possible range of the forces.

Examples of sensing elements suitable for the above purposes are strain gauges of N2AQ-XX-S061P-350 type produced by Measurement Group VISHAY, Raleigh, N.C., USA. Such a sensing element normally comprises a thin-film serpentine-type resistor, which can be connected to one arm of a bridge-type or a potentiometric electric measurement circuit.

The sensor 300 is identical to the aforementioned sensor 200. Therefore only end blocks 314, 316 and a beam 312 of the sensor 300 are designated in FIG. 2.

The end block 214 of the sensor 200 is positioned with respect to the upper plate 104 by means of set pins 250 and 252 inserted into openings 250*a* and 252*a* of the upper plate 104 through openings 250*b* and 252*b* of the lower plate 102 and openings 250*c* and 252*c* of the end block 214 (FIG. 2). The end block 214 is attached to the upper plate 104 by means of bolts 254 and 256 inserted through openings 254*a* and 256*a* of the lower plate 102, openings 254*b*, 256*b* of the end block 214, and screwed into threaded openings 254*c*, 256*c* of the upper plate 104.

The end block 216 of the sensor 200 is positioned with respect to the lower plate 102 by means of set pins 258 and 260 inserted into openings 258*a* and 260*a* of the lower plate 102 through openings 258*b* and 260*b* of the upper plate 104 and openings 258*c* and 260*c* of the end block 216. The end block 216 is attached to the lower plate 102 by means of bolts 262 and 264 inserted through openings 262*a* and 264*a* of the upper plate 104, openings 262*b*, 264*b* of the end block 216, and screwed into threaded openings 262*c*, 264*c* of the lower plate 102.

The end block 314 of the sensor 300 is positioned with respect to the lower plate 102 by means of set pins 266 and 268 inserted into openings 266*a* and 268*a* of the lower plate 102 through openings 266*b* and 268*b* of the upper plate 104 and openings 266*c* and 268*c* of the end block 314. The end block 314 is attached to the lower plate 102 by means of bolts 270 and 272 inserted through openings 270*a* and 272*a* of the upper plate 104, openings 270*b*, 272*b* of the end block 314, and screwed into threaded openings 270*c*, 272*c* of the lower plate 102.

The end block 316 of the sensor 300 is positioned with respect to the upper plate 104 by means of set pins 274 and 276 inserted into openings 274*a* and 276*a* of the upper plate 104 through openings 274*b* and 276*b* of the lower plate 102 and openings 274*c* and 276*c* of the end block 316. The end block 316 is attached to the upper plate 104 by means of bolts 278 and 280 inserted through openings 278*a* and 280*a* of the lower plate 102, openings 278*b*, 280*b* of the end block 316, and screwed into threaded openings 278*c*, 280*c* of the upper plate 104.

Reference numeral 281 designates a protective shield, which prevents access to the sensors from outside when the device shown in FIG. 2 is in an assembled state.

Figure 4:
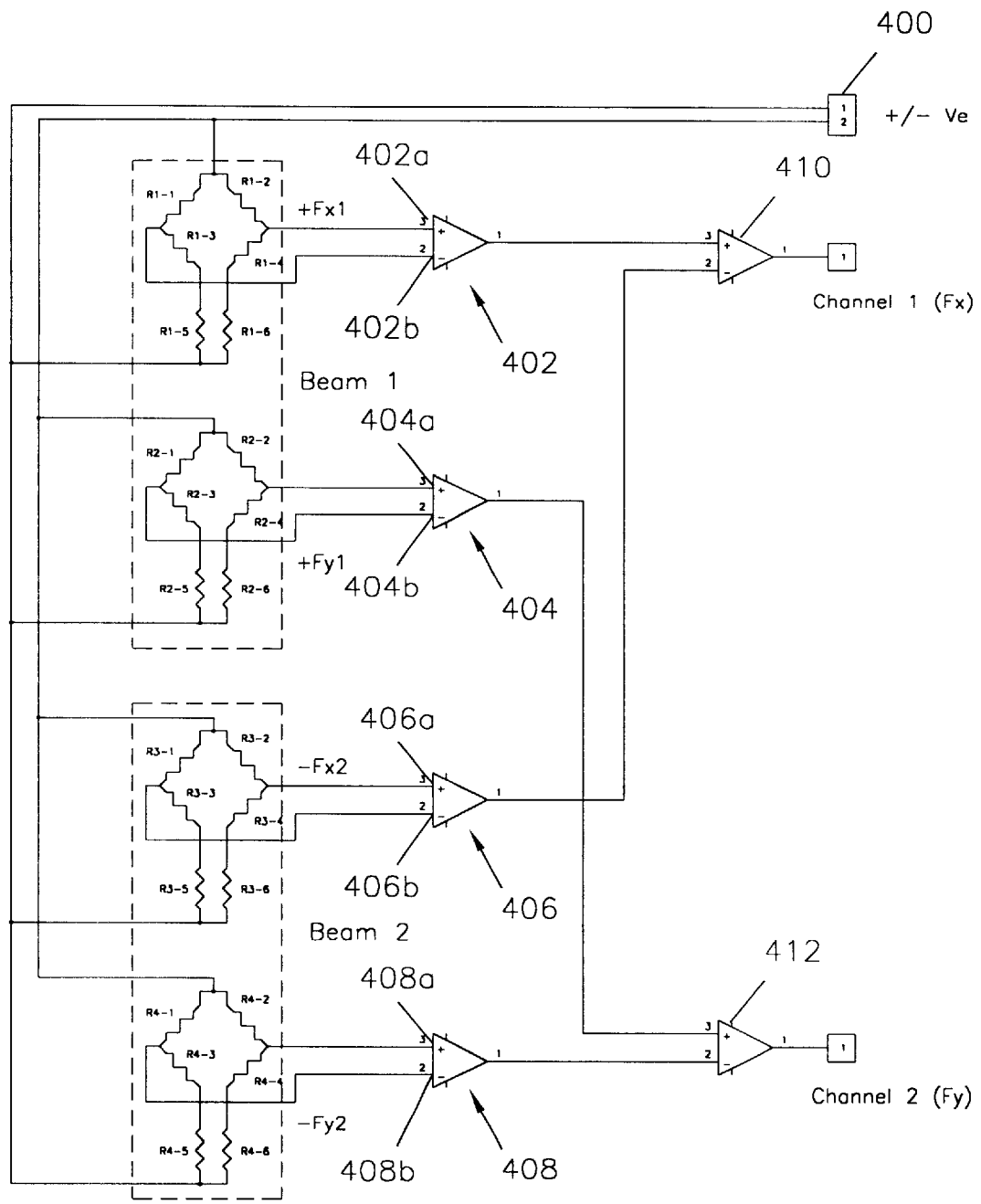
FIG. 4 is an example of an electric circuit for connection of double-force sensors to the registration and measurement apparatus.

An example of a bridge-type connection circuit for strain gauges 238*a*, 238*b*, 240*a*, 240*b* is shown in FIG. 4. In this circuit, R1-1 designates a pair of resistors corresponding to the strain gauge 238*a* of the sensor 200 shown in FIG. 3, whereas R1-2 designates a pair of resistors corresponding to the strain gauge 238*b* which is located on the side of the sensor 200 opposite to the side of the strain gauges 238*a* and which is not seen in the drawing. The pairs of resistors R1-1 and R1-2 form a first bridge. R1-3 and R1-4 designate balancing resistors for the first bridge. R2-1 designates a pair of resistors corresponding to the strain gauge 240*a* of the sensor 200 shown in FIG. 3, whereas R2-2 designates a pair of resistors corresponding to the strain gauge 240*b* which is located on the side of the sensor 200 opposite to the side of the strain gauge 240*a* and which is not seen in the drawing. The pairs of resistors R2-1 and R2-2 form a second bridge. Resistors R2-3 and R2-4 are balancing resistors for this second bridge.

R3-1 and R3-2 designate pairs of resistors, which form a third-bridge and which are located on the sensor 300 similarly to the pairs of resistors R1-1 and R1-2 of the beam 200. R3-3 and R3-4 are balancing resistors of the third bridge. R4-1 and R4-2 designate pairs of resistors, which form a fourth bridge and which are located on the sensor 300 similarly to the pairs of resistors R2-1 and R2-2 of the sensor 300. R4-3 and R4-4 are balancing resistors for the fourth bridge.

In the electric circuit of FIG. 4, reference numeral 400 designates a power source which is connected to each bridge formed by respective strain gauges and balancing resistors in both sensors 200 and 300. As shown in FIG. 4, both output leads of the first bridge formed by the resistors R1-1 and R1-2 are connected to a positive and a negative inputs 402*a* and 402*b*, respectively, of the first adder amplifier 402. Similarly, both output leads of the second bridge formed by the resistors R2-1 and R2-2 are connected to a positive and negative inputs 404*a* and 404*b*, respectively, of the second adder amplifier 404.

Similarly, both outputs of the third bridge formed by the resistors R3-1 and R3-2 are connected to a positive and a negative inputs 406*a* and 406*b*, respectively, of the third adder amplifier 406. Both outputs of the fourth bridge formed by the resistors R4-1 and R4-2 are connected to a positive and negative inputs 408*a* and 408*b*, respectively, of the fourth adder amplifier 408.

Outputs of the first amplifier 402 and of the third amplifier 406, which produce output signals corresponding to force $F_x$ acting in the direction of axis X and measured by both sensors 200 and 300, respectively, are supplied to a first output amplifier 410, whereas outputs of the second amplifier 404 and of the fourth amplifier 408, which produce output signals corresponding to force $F_y$ acting in the direction of axis Y and measured by both sensors 200 and 300, respectively, are supplied to a second output amplifier 412.

An output of the amplifier 410 is connected to channel 1 and an output of amplifier 412 is connected to channel 2 of the measurement and registration apparatus (not shown).

Attached to the lower plate 102 (FIG. 2) is a specimen mounting plate 282 for attaching an upper specimen 283 which is secured in a chuck 284 connected to mounting plate 282.

Mounting plate 282 is connected to lower plate 102 by bolts (not shown) which are screwed into threaded opening 287*a*, 287*b*, 287*c*, and 287*d* of the lower plate 102 via openings 288*a*, 288*b*. The upper specimen 283 is located in the geometrical center of the lower plate. It is assumed that the loading force and the reaction force pass through this point.

Operation of the device of the invention will now be described with reference to FIG. 5, which is a three-dimensional view illustrating both sensors in connection with forces applied to the sensors and measured by various strain gauges of both sensors.

In the course of testing, the moveable lower specimen 289 is brought into movement, e.g., into rotation, and then a loading force $F_x$ (FIG. 2) is applied to the sensor assembly from the loading unit of the tester (not shown) via the stationary upper plate 104. Strictly speaking, the upper specimen is not stationary, as it moves slightly together with the lower plate 102 when the beams of the sensors deform. However, for the sake of simplicity these movements of the upper specimen 283 are not taken into consideration and in the context of the present patent application the upper specimen 283 is considered as stationary.

Figure 1:
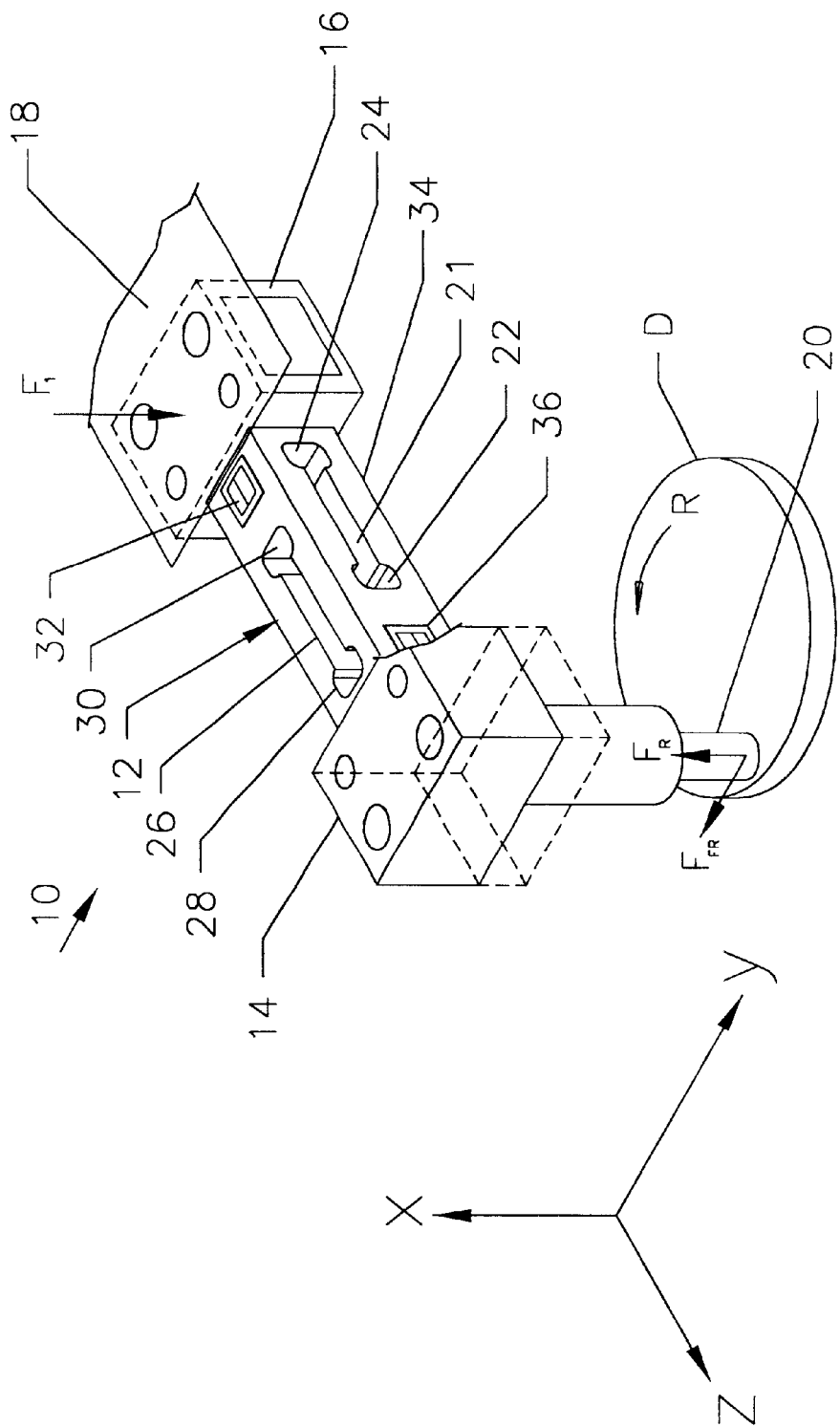
FIG. 1 is a three-dimensional view of a known device for force measurement in a friction tester.

When the upper specimen 283 comes into contact with the moving lower specimen 289, application of force $F_x$ causes interaction between the upper specimen 283 and the lower specimen 289. The aforementioned interaction generates a reaction force $F_R$ and a friction force $F_{FR}$ (FIG. 1). These forces deform the beams 212 and 312 of both sensors and hence the strain gauges. Since the sensors are sandwiched between the upper plate 104 and the lower plate 102 and are attached to both plates in manner shown and described in connection with FIG. 2, both sensors are subject to simultaneous equal deformations in two opposite directions for eliminating misbalance created in the measurement system when a single sensor is used. Each sensor deforms in the direction of axis X under the effect of a loading force $F_x$ measured in each sensor by two strain gauges located on opposite sides of the beam near one end of the beam and in direction of axis Y under the effect of a friction force measured in each sensor by another two strain gauges located on opposite sides of the beam, which are perpendicular to the sides of strain gauges for the loading force. Since both sensors 200 and 300 are sandwiched between two plates in diagonally symmetrical positions, they transmit forces between both plates and at the same time ensure limited freedom of movement between the plates to allow deformations caused by the applied forces.

Figure 5:
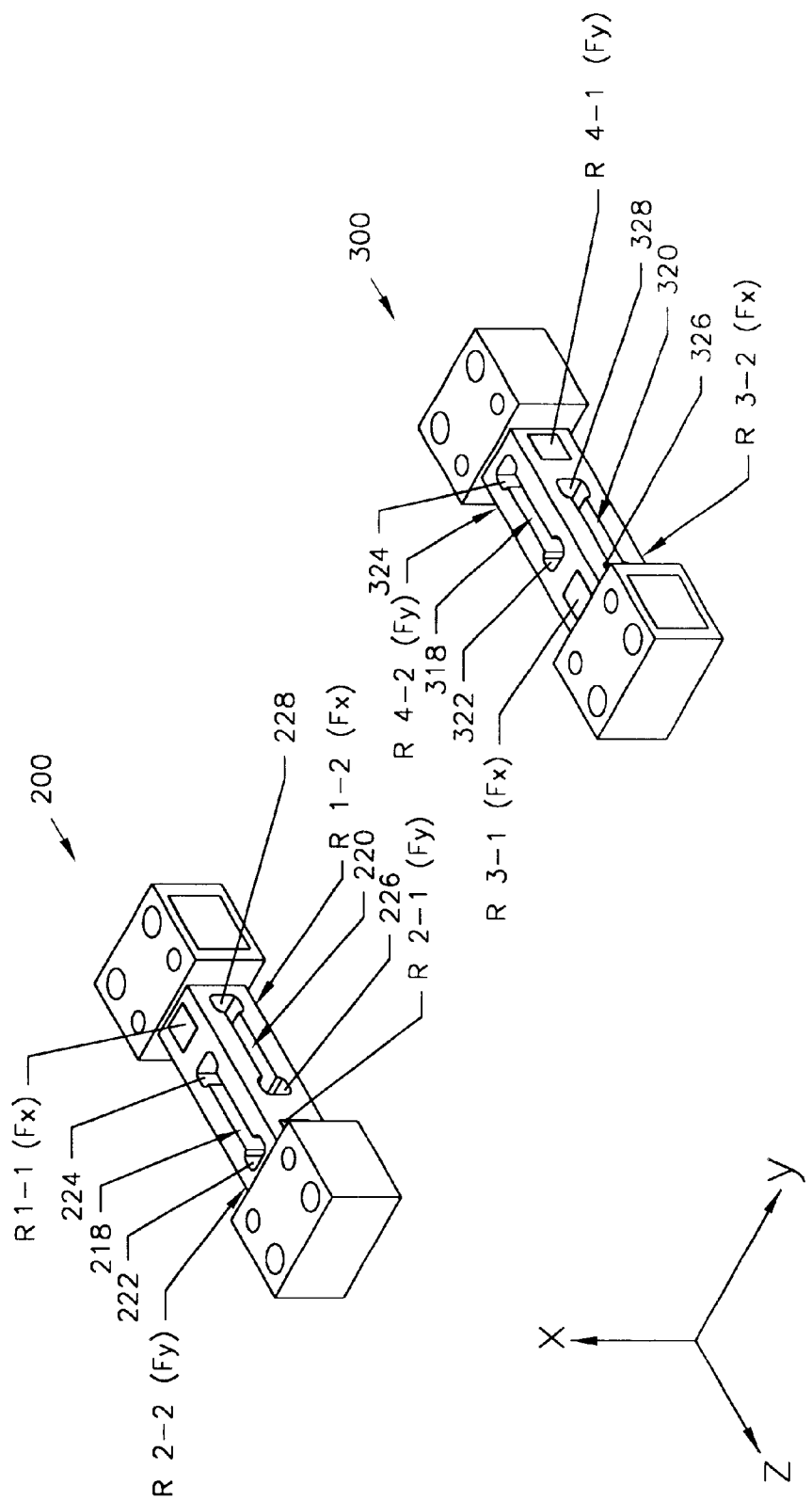
FIG. 5 is a three-dimensional view illustrating both sensors in connection with forces applied to the sensors and measured by various strain gauges of both sensors.

More specifically, due to the provision of the slots 218 and 220 (FIG. 5) with notches 222, 224 and 226, 228, respectively, in the sensor 200 and of the slots 318 and 320 with notches 322, 324 and 326, 328, respectively, in the sensor 300, the beams 212 and 312 are deformed under effect of force $F_x$ in a X-Z plane as a first parallelograms so that the materials of the beams are stretched on the sides of the resistors R1-1 and R3-1 and are compressed on the side of the resistors R1-2 and R3-2 (FIG. 5).

Friction force $F_{FR}$ acts in the direction of axis Y (FIG. 5) and deforms the beams 212 and 312 as second parallelograms in Z-Y plane so that the materials of the beams are stretched on the sides of resistors R2-1 and R4-1 and are compressed on the sides of resistors R2-2 and R4-2 (FIG. 5).

As the beams deform, the strain gauges also deform. These deformations change resistances of the resistors in the aforementioned bridges of the electric circuit shown in FIG. 4. As a result, resistors R1-1, R1-2 and R3-1, R3-2 measure force $F_x$, whereas resistors R2-1, R2-2 and R4-1, R4-2 measure force $F_y$.

Due to the fact that each bridge is formed by pairs of resistors one of which always increases in its resistance while the other decreases, or vice verse, the electric circuit shown in FIG. 4 improves sensitivity of the measurement system approximately by a factor of 2. Furthermore, output signals which correspond to one and the same force, e.g., force $F_x$, also are summed to form an electric signal of a doubled magnitude. Thus, increased electric signals corresponding to respective forces are supplied to the measuring and registering system (not shown).

The invention has been shown and described with reference to a specific embodiment which should be construed only as an example and does not limit the scope of practical applications of the invention. Therefore any changes and modifications in materials, shapes, electric diagrams and their components are possible, provided these changes and modifications do not depart from the scope of the patent claims. For example, the electric bridge circuits shown in FIG. 4 can be circuits operating on a.c. current or on d.c. current. The a.c. bridge can be a resonance type bridge circuit. The strain gauge resistors can be represented by a part of a potentiometric circuit. The resistor-type strain gauges can be replaced by capacitive-type strain gauges. The sensing elements of such type can be a part of a dilatometric measurement circuit in which deformation of the gauge proportionally changes capacity of the sensing element. Although the sensors were mentioned for use in measuring a load force and a friction force, it is understood that they can be used for other purposes, such as measuring bending moments in two directions. In association with known masses properly attached to the sensors, the latter can be used as acceleration and velocity sensors. The solid end blocks 214, 216 and 314, 316 can be fixed and attached to fixation and actuating elements in a variety of modes. The lower specimen can perform reciprocating movements and the test can be carried out in oil and/or at an elevated temperature. The beams may have an elliptical, or any other cross-section and the direction of applied forces may not necessarily be mutually perpendicular. The slots and notches may have shapes different from those shown in the drawings. The beams themselves can be assembled from several parts. The beams can be formed without notches, i.e., only with two pairs of slots. The deformable beams not necessarily should be solid bodies with the notches and slots and can be formed by four or more deformable rods, plates, or tubes which together may form two mutually perpendicular parallelograms. The strain gauges contained in one bridge circuit may have any other suitable location, e.g., on the same side of the beam instead of opposite sides of the beam.

What is claimed is:

1. A device for measuring a first force acting in one direction and a second force acting in a direction which is different from said one direction and is not parallel thereto, said device comprising:
   a first mounting member;
   a second mounting member;
   a first flexible member having a first end and a second end opposite to said first end, said first end being attached to said first mounting member and said second end being attached to said second mounting member;
   a second flexible member, which is identical to said first flexible member, is arranged parallel thereto and has a first end, which corresponds to said first end of said first flexible member, attached to said second mounting member, and a second end opposite to said first end of said second flexible member, said second end of said second flexible member corresponding to said second end of said first flexible member, and being attached to said first mounting member; and
   deformation sensitive means for measuring deformations of said first flexible member and of said second flexible member in terms of said first force and said second force respectively, said first flexible member and said second flexible member being deformed simultaneously by equal amounts and in mutually opposite directions.

2. The device of claim 1, wherein said first force is a loading force, said second force is a friction force, said first mounting member is a first plate, said second mounting member is a second plate, said first flexible member and said second flexible member comprising deformable beams sandwiched between said first plate and said second plate.

3. The device of claim 2, wherein each of said deformable beams having a first end and a second end and comprises:
   a first pair of deformable portions for deforming said deformable beam in said one direction and a second pair of deformable portions for deforming said deformable beam in a second direction which is different from said one direction;
   a first pair of deformation sensitive elements attached to opposite sides of one of said deformable portions of said first pair and a second pair of deformation sensitive elements attached to opposite sides of one of said deformable portions of said second pair;
   said first pair of deformable portions and said second pair of deformable portions being formed in said deformable beam by a first pair of through holes with a first through slot which interconnects said first pair of through holes, said first pair of through holes and said first through slot passing through said deformable beam in said second direction, and by a second pair of through holes with a second through slot which interconnects said second pair of said through holes, said second through holes and said second through slot passing through said deformable beam in said one direction; each through hole of said first pair of through holes and of said second pair of through holes having a longitudinal axis;
   said first pair of said through holes comprising a first through hole located close to said first end of said deformable beam and having said longitudinal axis in said second direction and a second through hole located close to said second end of said deformable beam and having said longitudinal axis in said second direction;
   said second pair of said through holes comprising a third through hole located close to said first end of said deformable beam and having said longitudinal axis in said first direction and a fourth through hole located close to said second end of said deformable beam and having said longitudinal axis in said first direction;
   said second through hole and said third through hole being located between said first through hole and said fourth through hole;
   said second through hole being located between said third through hole and said fourth through hole;
   said third through hole being located between said first through hole and said second through hole.

4. The device of claim 3, wherein each of said deformable beams further comprises a first beam attachment means connected to said first end of said deformable beam and a second attachment means connected to said second end of said deformable beam.

5. The device of claim 1, wherein each of said deformation sensitive means comprises a strain gauge.

6. The device of claim 3, wherein each of said deformation sensitive elements comprises a strain gauge.

7. The device of claim 6, wherein said first direction and said second direction are mutually perpendicular directions.

8. The device of claim 1, wherein said one direction and said direction different from said one direction are mutually perpendicular directions.

9. The device of claim 2, wherein each of said beams has a rectangular cross section.

10. The device of claim 1, wherein each of said flexible members has a longitudinal axis and comprises: a first parallelogram deformable in said first direction; a second parallelogram deformable in said second direction, said first parallelogram being at least partially overlapped with said second parallelogram along said longitudinal axis;

said first parallelogram being formed at least by a first through slot passing through said flexible member in said second direction, and said second parallelogram is formed at least by a second through slot passing through said flexible member in said first, said first through slot and said second through slot each having a first end and a second end.

11. The device of claim 10, wherein each of said flexible members further comprises a first pair of through notches which are wider than said first slot and which are connected to both ends of said first slot and a second pair of through notches which are wider than said second slot and which are connected to both ends of said second slot.

12. The device of claim 10, wherein in each of said flexible members said deformation sensitive means comprise:

a first pair of strain gauges located at said first end of said first through slot and on opposite sides of said first parallelogram for measuring said first force; and a second pair of strain gauges located at said second end of said first through slot and on the opposite sides of said second parallelogram for measuring said second force.

13. The device of claim 12, further comprising an electric circuit, wherein in each of said flexible members said first pair of strain gauges forms a first bridge for measuring said first force, whereas said second pair of strain gauges forms a second bridge for measuring said second force.

14. A method of measuring a first force acting in a first direction and a second force acting in a second direction which is not parallel to and is different from said first direction, said method comprising:

providing a bidirectional force measurement device having a first plate, a second plate, a first deformable member, having a first end and a second end, and a second deformable member, having a first end and a second end, said first deformable member and said second deformable member being sandwiched between said first plate and said second plate in a diagonally symmetrical positions with respect to each other so that said first end of each of said deformable members is attached to said first plate and said second end is attached to said second plate;

providing each of said deformable members with first measuring means for measuring said first force and with second measurement means for measuring said second force;

applying said first force to a plate selected from said first plate and said second plate;

applying said second force to a plate selected said first plate and said second plate; and measuring said first force and said second force simultaneously in both of said deformable members.

15. The method of claim 14, comprising the step of using said bidirectional force measurement device in a friction tester having a loading unit, a first specimen, and a second specimen, said first force being a loading force and said second force being a friction force, said method further comprising:

attaching said first plate to said loading unit of said friction tester;

attaching said first specimen to said second plate;

causing a relative movement between said first specimen and said second specimen while applying said loading force to said first plate thus developing said friction force;

causing deformations of said first deformable member and of said second deformable member under effect of said loading force and said friction force; and measuring deformations in terms of said loading force and said friction force, respectively.

16. The method of claim 15, comprising:

forming each of said deformable members as a first deformable parallelogram deformable by said loading force in said first direction and a second deformable parallelogram deformable by said friction force in said second direction, said first deformable parallelogram and said second deformable parallelogram being at least partially overlapped.

* * * * *